US010660706B2

(12) United States Patent
Mozes et al.

(10) Patent No.: US 10,660,706 B2
(45) Date of Patent: May 26, 2020

(54) SURGICAL ROBOT SYSTEM FOR INTEGRATED SURGICAL PLANNING AND IMPLANT PREPARATION, AND ASSOCIATED METHOD

(71) Applicant: NEOCIS, INC., Miami Beach, FL (US)

(72) Inventors: Alon Mozes, Miami Beach, FL (US); Juan Salcedo, Miami, FL (US); Jeffrey Ganeles, Boca Raton, FL (US); Federico Grande, Stuart, FL (US)

(73) Assignee: NEOCIS, INC., Miami, FL (US)

( * ) Notice: Subject to any disclaimer, the term of this patent is extended or adjusted under 35 U.S.C. 154(b) by 87 days.

(21) Appl. No.: 15/253,508

(22) Filed: Aug. 31, 2016

(65) Prior Publication Data

US 2016/0367343 A1   Dec. 22, 2016

Related U.S. Application Data

(63) Continuation of application No. PCT/US2015/018775, filed on Mar. 4, 2015.
(Continued)

(51) Int. Cl.
*A61C 8/00* (2006.01)
*A61B 34/10* (2016.01)
*A61C 1/08* (2006.01)
*A61B 34/20* (2016.01)
*G16H 20/40* (2018.01)
*A61C 5/77* (2017.01)
*A61B 90/00* (2016.01)

(52) U.S. Cl.
CPC .............. *A61B 34/10* (2016.02); *A61B 34/20* (2016.02); *A61C 1/084* (2013.01); *A61C 8/0089* (2013.01); *A61B 2090/3983* (2016.02); *A61C 5/77* (2017.02); *G16H 20/40* (2018.01)

(58) Field of Classification Search
CPC ............................ A61C 9/0046; A61C 9/008
See application file for complete search history.

(56) References Cited

U.S. PATENT DOCUMENTS

| 5,343,391 A * | 8/1994 | Mushabac | A61C 13/0004 |
| | | | 433/76 |
| 2002/0077542 A1* | 6/2002 | Vilsmeier | A61C 1/084 |
| | | | 600/424 |

(Continued)

*Primary Examiner* — Ralph A Lewis
(74) *Attorney, Agent, or Firm* — Womble Bond Dickinson (US) LLP

(57) ABSTRACT

Dental implantation systems and methods are provided, including a site preparation device for preparing a site within a patient's mouth for receiving an anchor portion of a dental implant. An implant preparation device forms a crown portion of the dental implant for reception by the anchor portion. A guidance device communicates with a fiducial marker engaged with the patient's mouth, to interchangeably receive the site and implant preparation devices, and to guide the site and/or implant preparation device, relative to the fiducial marker, in conjunction with manipulation thereof by a user. A planning device communicates with and via the guidance device, and determines an arrangement of the dental implant at the site, to direct the site preparation device to prepare the site to receive the dental implant arrangement, and to direct the implant preparation device to prepare the crown portion for receipt by the anchor portion.

12 Claims, 7 Drawing Sheets

Related U.S. Application Data

Figure 1A:
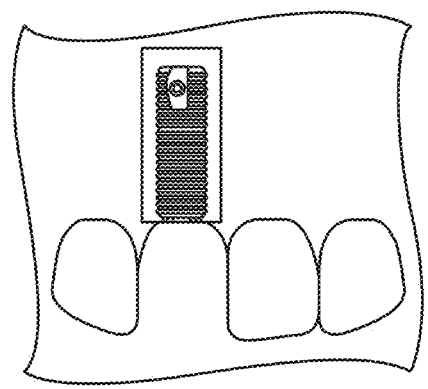

(60) Provisional application No. 61/947,795, filed on Mar. 4, 2014.

(56) References Cited

U.S. PATENT DOCUMENTS

| | | | | |
|---|---|---|---|---|
| 2005/0163342 A1* | 7/2005 | Persky | ............... | A61B 6/14 382/103 |
| 2009/0253095 A1* | 10/2009 | Salcedo | ............... | A61B 1/24 433/75 |
| 2014/0199650 A1* | 7/2014 | Moffson | ............... | A61C 1/082 433/27 |
| 2016/0367343 A1* | 12/2016 | Mozes | ............... | A61C 8/0089 |

* cited by examiner

SURGICAL ROBOT SYSTEM FOR INTEGRATED SURGICAL PLANNING AND IMPLANT PREPARATION, AND ASSOCIATED METHOD

CROSS REFERENCE TO RELATED APPLICATIONS

This application is a continuation of International Application No. PCT/US2015/018775, filed Mar. 4, 2015, which International Application was published by the International Bureau in English on Sep. 11, 2015, which claims priority to U.S. Provisional Application No. 61/947,795, filed on Mar. 4, 2014, which all are incorporated by reference herein in their entirety.

BACKGROUND

Field of the Disclosure

The present application relates to surgical robots and associated guidance systems and, more particularly, to a guided surgical robot system used, for example, in dental surgery, wherein the system is also configured to facilitate pre-procedure planning and data collection, as well as to prepare implements and other apparatuses for use in the surgical procedure.

Description of Related Art

A dental implant procedure involves several aspects: making the diagnosis, planning the position of the implant, surgically milling the anatomy and placing the implant (i.e., an anchoring post), and then attaching the abutment and crown (i.e., prosthetic tooth/teeth). Some existing systems may include provisions for planning and executing one or more aspects of such a surgical procedure. However, the formation/creation of the crown portion of the dental implant is often conducted by a separate system and in a separate operation. For example, some systems may require a surgeon to first develop a surgical plan, via software, which may involve, for instance, a drilling operation. In such instances, when the plan is finalized, an outside vendor or laboratory is likely retained to form a drill guide for intra-operative use, according to the surgical plan. In such instances, the crown(s) are likely produced/milled by the same vendor/lab, but the milling machines for making such crowns are separate and discrete from the surgical procedure itself.

Some surgical systems, such as dental implantation surgical systems, may implement planning of the surgical procedure based on non-invasive imaging of the planned surgical site (i.e., via a CT scan). The result of the plan, namely the collected image(s) of the surgical site or patient anatomy, can thus be used, for example, for diagnosis, for manufacturing a drill guide, or for guiding haptic or autonomous robotic systems. However, in some instances, the CT image (or the MRI image or other reference image used for surgical planning purposes) may not include all of the necessary information for allowing sound clinical judgment, or the patient's anatomy may change in the time between the imaging procedure and the actual surgical procedure.

As such, it may be desirable to provide a more integrated surgical system and method having the capability of performing more and different aspects of the intended surgical procedure, in relation to a known reference in relation to the patient. Further, it may also be desirable for such a system and method to be capable of providing real-time feedback and real-time plan update functionality while live on a patient and/or during the surgical procedure itself.

SUMMARY OF THE DISCLOSURE

The above and other needs are met by aspects of the present disclosure which, in one particular aspect, provides a dental implantation system and associated method, wherein such a system comprises a site preparation device adapted to prepare a site within a mouth of a patient for receiving an anchor portion of a dental implant, and an implant preparation device configured to form a crown portion of the dental implant, wherein the crown portion is configured to be received by the anchor portion, with the anchor portion securing the crown portion within the mouth of the patient. A guidance device, including a processor, is configured to be in communication with a fiducial marker adapted to be engaged with the mouth of the patient. The guidance device is also configured to interchangeably receive the site preparation device and the implant preparation device, and to guide one of the site preparation device and the implant preparation device, relative to the fiducial marker, in conjunction with manipulation of the one of the site preparation device and the implant preparation device by a user. A planning device, including a processor, is configured to be in communication with the guidance device. The planning device is further configured to determine an arrangement of the dental implant at the site in the mouth of the patient, to direct the site preparation device via the guidance device to prepare the site to receive the dental implant arrangement, and to direct the implant preparation device via the guidance device to prepare the crown portion for receipt by the anchor portion in accordance with the dental implant arrangement.

Another aspect provides a dental implantation system and associated method, wherein such a system comprises a patient-engaging device adapted to interact with a site within a mouth of a patient, and a guidance device, including a processor, wherein the guidance device is configured to be in communication with a fiducial marker adapted to be engaged with the mouth of the patient. The guidance device is configured to receive the patient-engaging device, and to guide the patient-engaging device relative to the fiducial marker, in conjunction with manipulation of the patient-engaging device by a user. A display device is configured to display a real-time representation of the patient-engaging device in relation to a representation of the mouth of the patient during manipulation of the patient-engaging device. A planning device, including a processor, is configured to be in communication with the guidance device and the display device. The planning device is configured to monitor manipulation of the patient-engaging device in relation to the mouth of the patient, at least partially via the guidance device, and to direct information associated therewith to the display device.

The present disclosure thus includes, without limitation, the following example embodiments:

Example Embodiment 1: A dental implantation system, wherein such a system comprises a site preparation device adapted to prepare a site within a mouth of a patient for receiving an anchor portion of a dental implant; an implant preparation device configured to form a crown portion of the dental implant, the crown portion being configured to be received by the anchor portion, and the anchor portion securing the crown portion within the mouth of the patient; a guidance device including a processor and configured to be in communication with a fiducial marker adapted to be engaged with the mouth of the patient, with the guidance device being configured to interchangeably receive the site preparation device and the implant preparation device, and to guide one of the site preparation device and the implant preparation device, relative to the fiducial marker, in conjunction with manipulation of the one of the site preparation device and the implant preparation device by a user; and a planning device including a processor, and configured to be in communication with the guidance device, with the planning device being configured to determine an arrangement of the dental implant at the site in the mouth of the patient, to direct the site preparation device via the guidance device to prepare the site to receive the dental implant arrangement, and to direct the implant preparation device via the guidance device to prepare the crown portion for receipt by the anchor portion in accordance with the dental implant arrangement.

Example Embodiment 2: The system of any preceding or subsequent example embodiment, or combinations thereof, further comprising a splint device adapted to engage the mouth of the patient to form the fiducial marker.

Example Embodiment 3: The system of any preceding or subsequent example embodiment, or combinations thereof, further comprising an arm member in communication with the guidance device and responsive thereto to guide one of the site preparation device, the implant preparation device, and the patient-engaging device.

Example Embodiment 4: The system of any preceding or subsequent example embodiment, or combinations thereof, wherein the arm member comprises an articulating arm member configured to determine a range of motion of the one of the site preparation device, the implant preparation device, and the patient-engaging device.

Example Embodiment 5: The system of any preceding or subsequent example embodiment, or combinations thereof, wherein the guidance device is further configured to interchangeably receive an implantation device, in addition to the site preparation device and the implant preparation device, and to guide the implantation device, relative to the fiducial marker, and in conjunction with manipulation of the implantation device by the user, to implant the dental implant within the patient's mouth.

Example Embodiment 6: A dental implantation system, wherein such a system comprises a patient-engaging device adapted to interact with a site within a mouth of a patient; a guidance device including a processor and configured to be in communication with a fiducial marker adapted to be engaged with the mouth of the patient, with the guidance device being configured to receive the patient-engaging device, and to guide the patient-engaging device relative to the fiducial marker, in conjunction with manipulation of the patient-engaging device by a user; a display device configured to display a real-time representation of the patient-engaging device in relation to a representation of the mouth of the patient during manipulation of the patient-engaging device; and a planning device including a processor, and configured to be in communication with the guidance device and the display device, with the planning device being configured to monitor manipulation of the patient-engaging device in relation to the mouth of the patient, at least partially via the guidance device, and to direct information associated therewith to the display device.

Example Embodiment 7: The system of any preceding or subsequent example embodiment, or combinations thereof, wherein the planning device is further configured to form a dental implantation plan associated with the mouth of the patient.

Example Embodiment 8: The system of any preceding or subsequent example embodiment, or combinations thereof, wherein the planning device is further configured to update the dental implantation plan at least partially in real-time relation to the monitored manipulation of the patient-engaging device.

Example Embodiment 9: The system of any preceding or subsequent example embodiment, or combinations thereof, wherein the planning device is further configured to finalize the dental implantation plan when further update thereof is not required.

Example Embodiment 10: The system of any preceding or subsequent example embodiment, or combinations thereof, wherein the planning device is further configured to guide the patient-engaging device in relation to the mouth of the patient according to the dental implantation plan.

Example Embodiment 11: The system of any preceding or subsequent example embodiment, or combinations thereof, wherein the planning device is further configured to direct a preparation device to prepare a dental implant, according to the dental implantation plan, for implantation in the mouth of the patient.

Example Embodiment 12: The system of any preceding or subsequent example embodiment, or combinations thereof, further comprising a splint device adapted to engage the mouth of the patient to form the fiducial marker.

Example Embodiment 13: The system of any preceding or subsequent example embodiment, or combinations thereof, further comprising an arm member in communication with the guidance device and responsive thereto to guide one of the site preparation device, the implant preparation device, and the patient-engaging device.

Example Embodiment 14: The system of any preceding or subsequent example embodiment, or combinations thereof, wherein the arm member comprises an articulating arm member configured to determine a range of motion of the one of the site preparation device, the implant preparation device, and the patient-engaging device.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 1B:
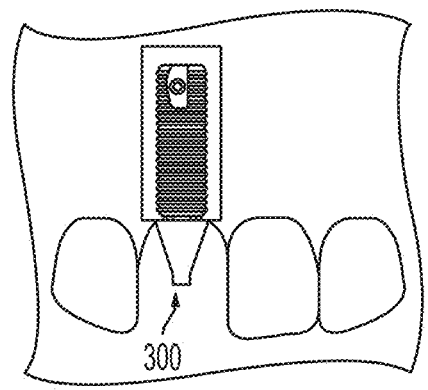
Figure 1C:
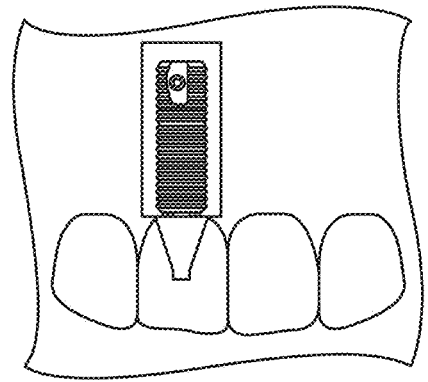
Figure 2:
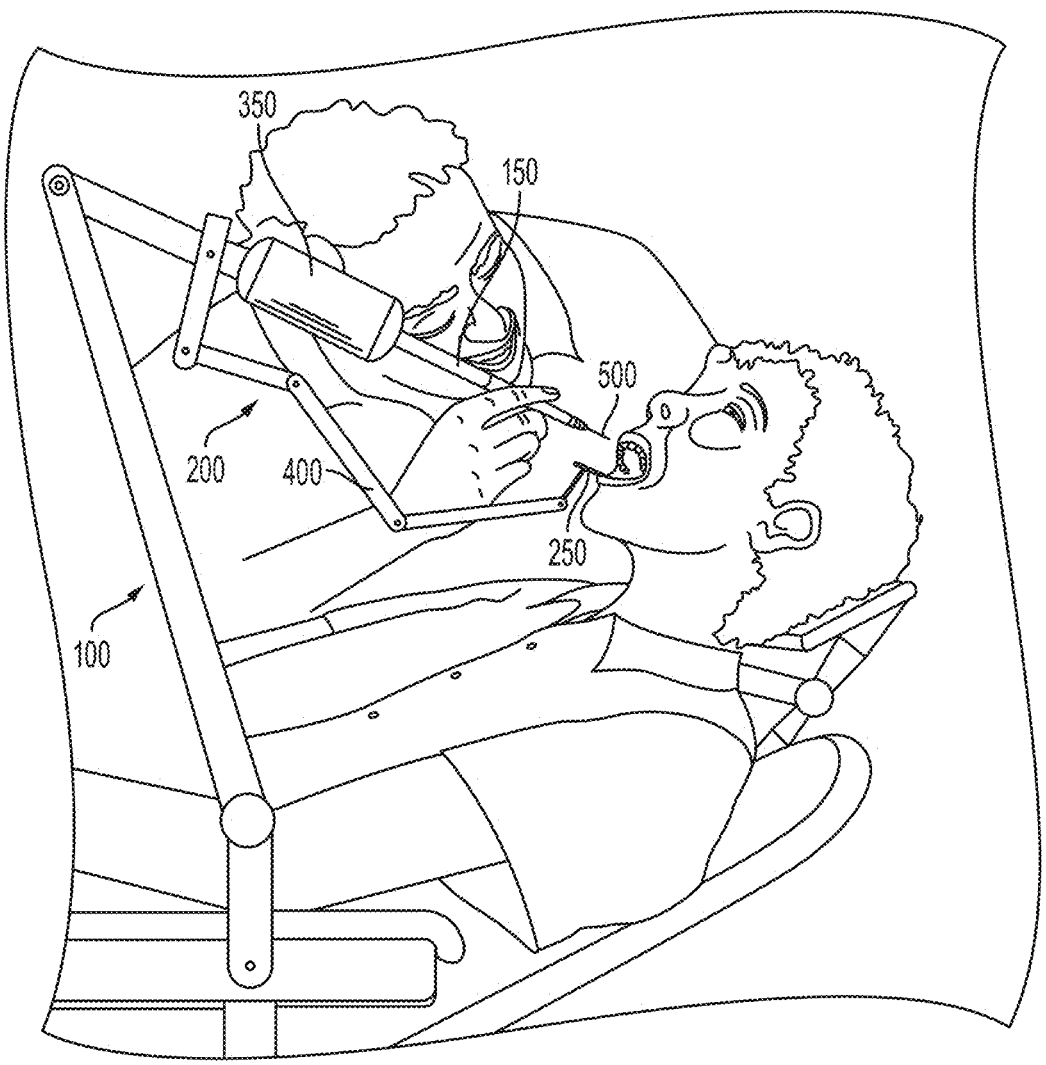
Figure 3:
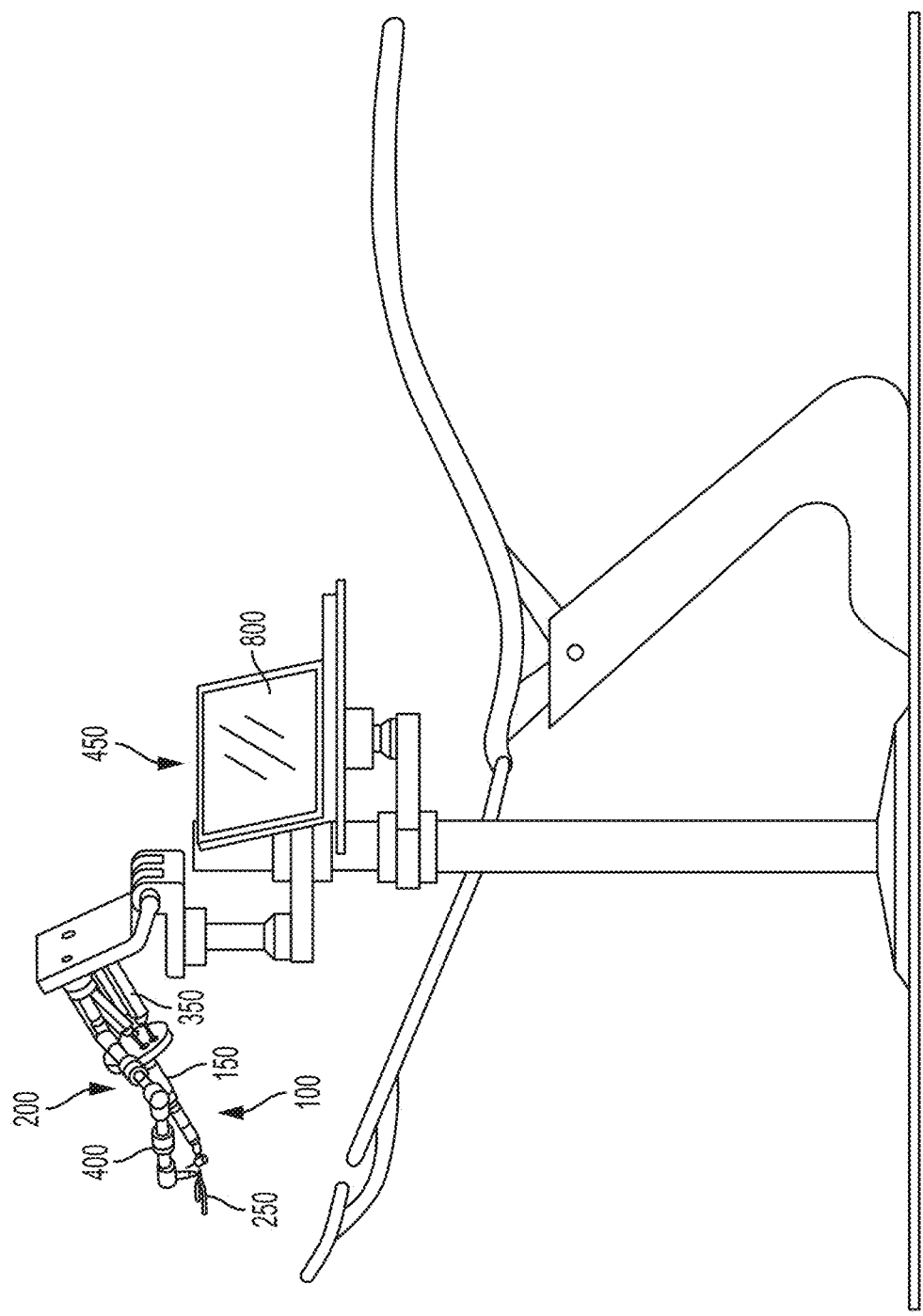
Figure 4:
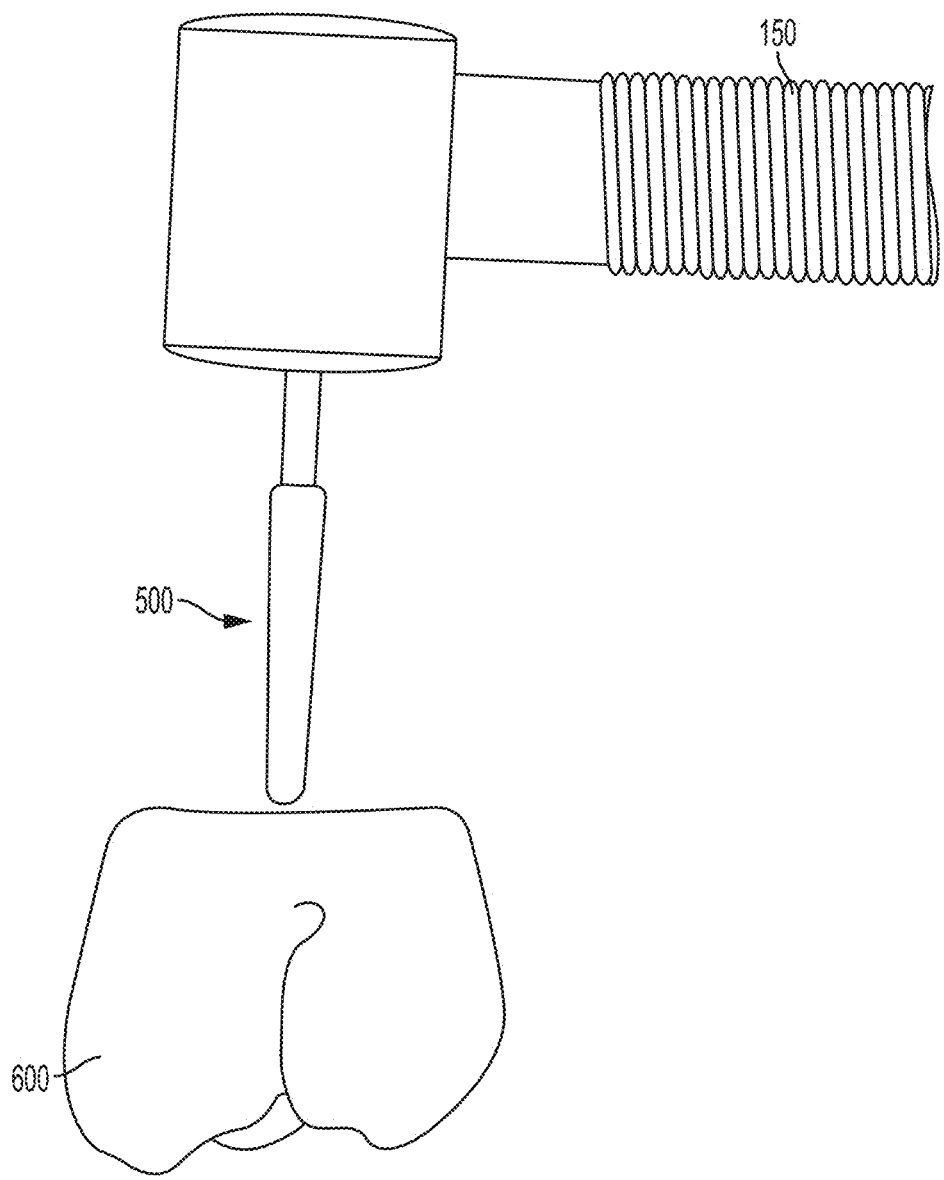
Figure 5A:
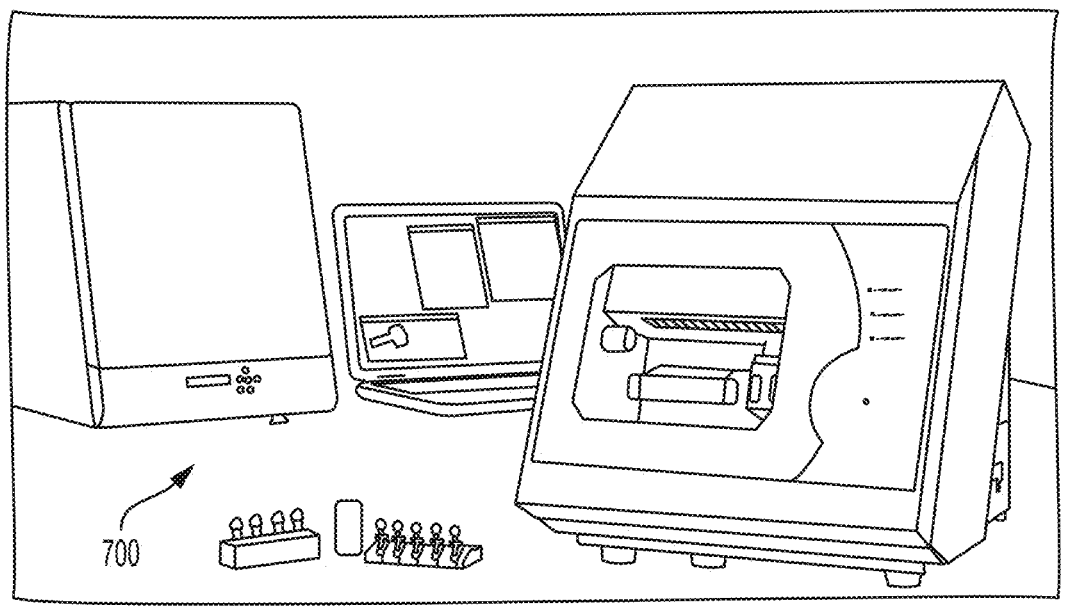
Figure 5B:
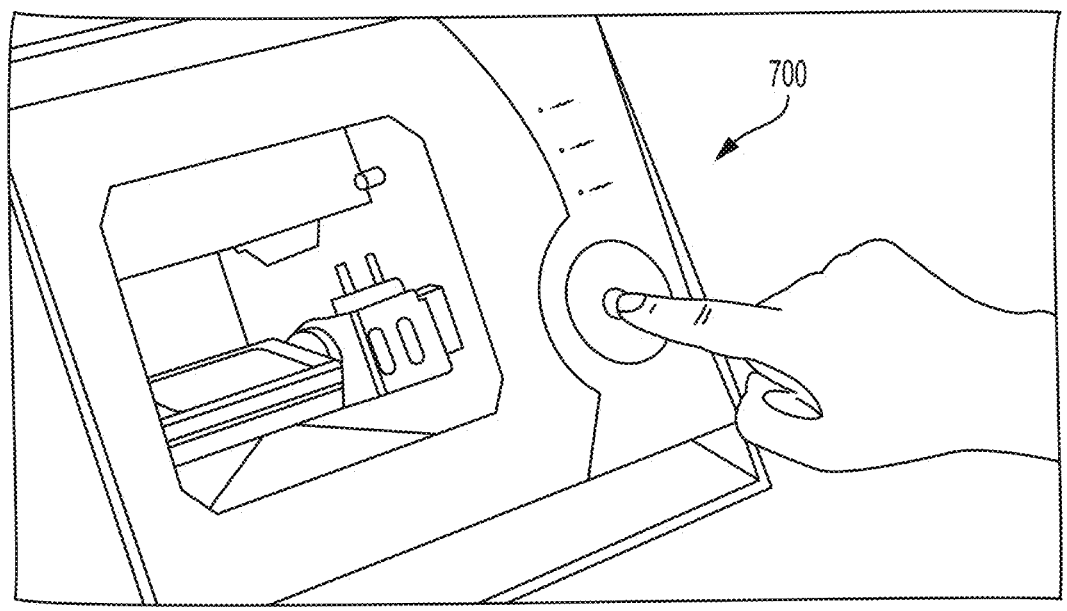
Figure 5C:
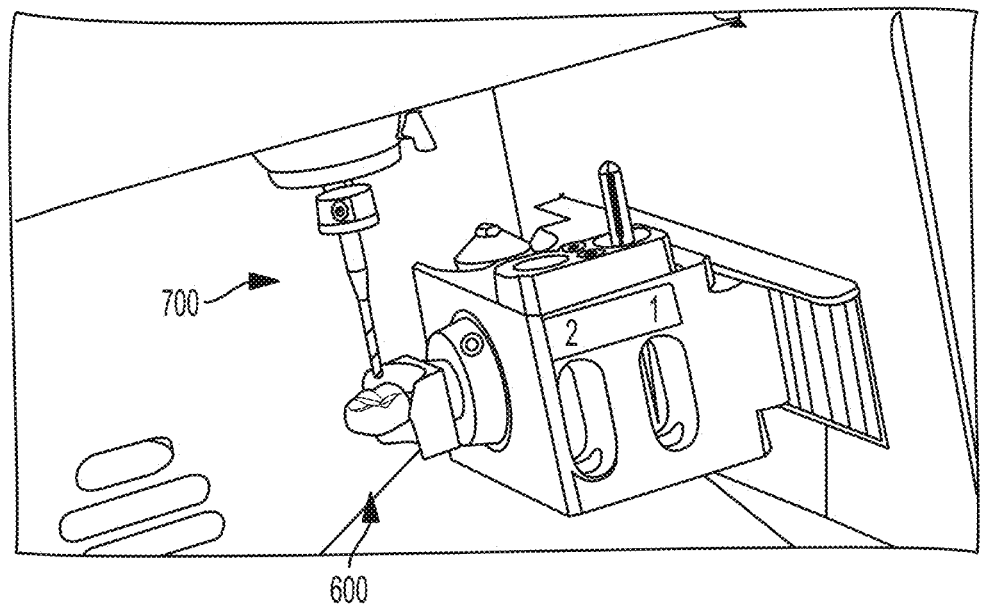
Figure 5D:
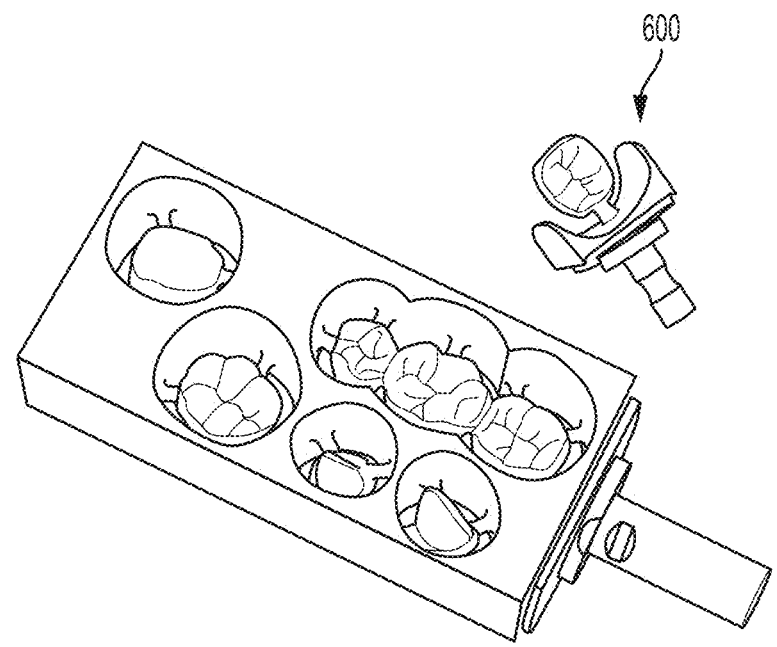
Figure 6:
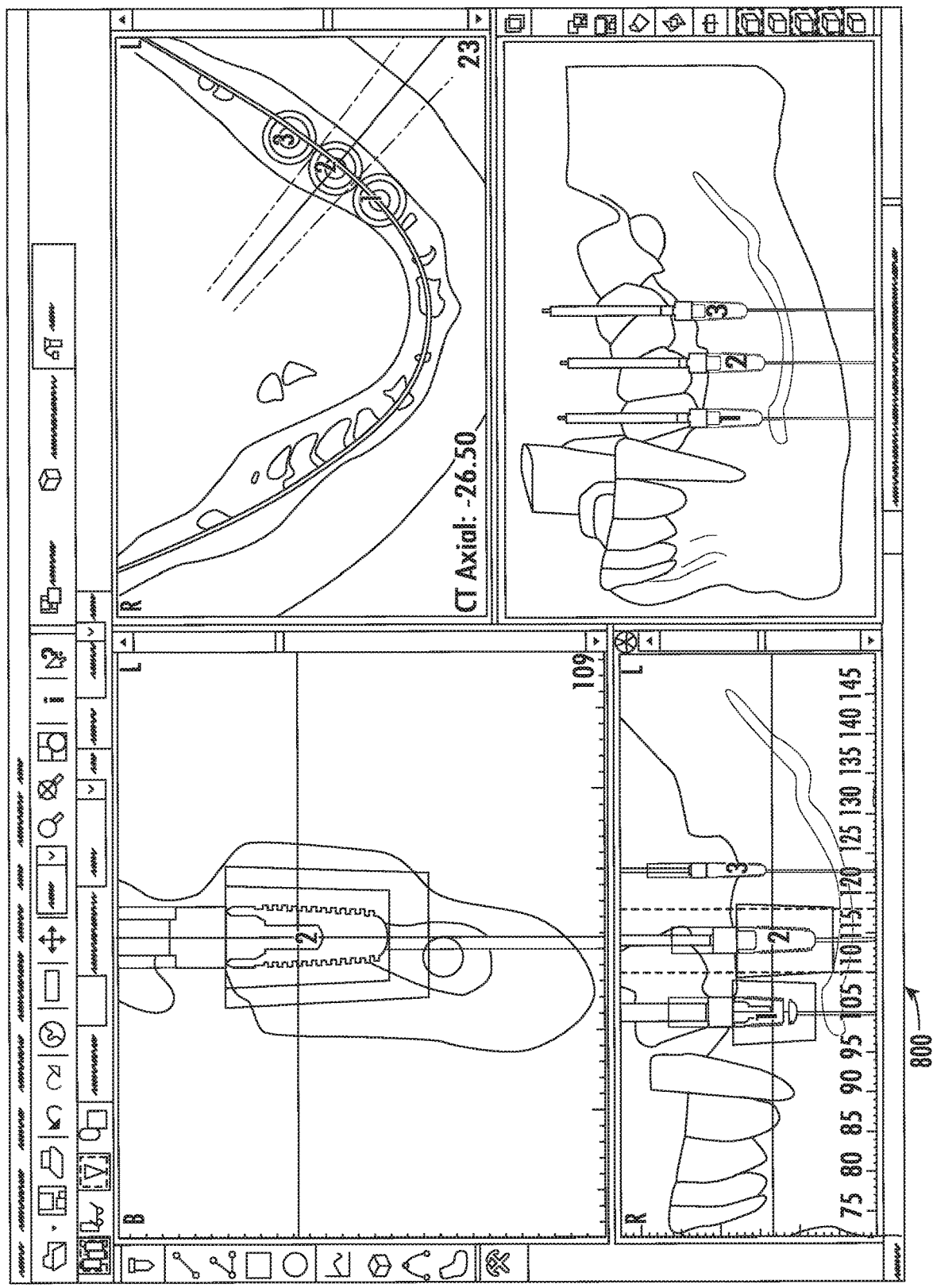

Having thus described the disclosure in general terms, reference will now be made to the accompanying drawings, which are not necessarily drawn to scale, and wherein:

FIGS. 1A-1C schematically illustrate a dental implantation procedure with respect to the mouth of a patient;

FIGS. 2 and 3 schematically illustrate a dental implantation system, according to various aspects of the present disclosure;

FIG. 4 schematically illustrates a procedure for preparing a prosthetic member with a dental implantation system, according to one aspect of the present disclosure; and FIGS. 5A-5D schematically illustrate an apparatus and method for forming a prosthetic member for a dental implantation procedure, according to one aspect of the present disclosure;

FIG. 6 schematically illustrates an apparatus and method for providing a representation of the patient-engaging device in relation to a representation of the mouth of the patient during manipulation of the patient-engaging device, according to one aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Various aspects of the present disclosure are based on a guided surgical robotic system and method such as that disclosed, for example, in U.S. Patent Application Publication No. US 2009.0253095 to Salcedo et al. and assigned to Neocis, also the assignee of the present application. The disclosure of US 2009/0253095 to Salcedo et al. is thus incorporated by reference herein.

In this regard, a dental implantation procedure generally involves an invasive incision into the gum of the patient in order to allow the practitioner to view the underlying jawbone structure. A hole is then drilled into the jawbone structure, into which a dental implant is placed (see, e.g., FIG. 1A). In some instances, the dental implant may be shaped, for example, like a screw or other threaded member. Once the dental implant is inserted into the jawbone structure, an external post is attached to the dental implant (see, e.g., FIG. 1B), and a prosthetic cap (i.e., a crown or tooth reproduction) attached to the post (see, e.g., FIG. 1C). With computerized tomography (CT) and other imaging scans becoming more common, the practitioner may be able to graphically visualize the jawbone structure, without or before the invasive incision. However, the alignment of the dental implant with respect to the jawbone structure and/or relative to other implants or teeth may be an important factor in determining, for example, the life of the dental implant, the appearance thereof, and the comfort to the patient. If the dental implant is poorly or otherwise not optimally placed, the dental implant can undesirably fail (or at least have a shorter service life), may undesirably cause other teeth or dental implants to be compromised, and/or damage proximal nerves.

FIGS. 2 and 3 thus illustrate various aspects of a dental implantation system according to the present disclosure, the system being generally indicated by the numeral 100. As previously indicated, current dental implantation procedures generally involve an imaging step, wherein CT or other appropriate images of the patient's jaw structure are obtained, and any anomalies diagnosed (i.e., whether the patient requires bone grafts to prepare the implant area). The practitioner then corrects any anomalies and proceeds with the invasive implant procedure based on the conditions associated with the patient's jaw structure, once the appropriate incisions have been made in the patient's gum. In this regard, one skilled in the art will appreciate that, though the present disclosure provides some exemplary aspects of the various systems and methods implemented with respect to the jaw structure of a patient, the various systems and method disclosed herein may be readily applicable, or otherwise readily adaptable, to other surgical procedures that are proximal to or otherwise capable of being correlated with the fiducial marker associated with the engagement between a splint or other engaging member, and the jaw structure of the patient, as otherwise disclosed herein (i.e., brain surgery, skull surgery, ENT surgery, or any other surgical procedure associated with the head/skull structure of the patient).

A dental implantation system 100 according to various aspects of the present disclosure addresses the subjective aspects of current dental implantation procedures by providing a guided patient-engaging or interaction device 150 (otherwise referred to herein as a "cutting device" or "drilling device" or "site preparation device" or "implantation device" when the patient-engaging device 150 is configured for a particular corresponding purpose) configured to be guided with respect to the invasive portion, or at least the patient-interacting portion, of the dental implant procedure (i.e., to "prepare" the site within or otherwise engage the patient's mouth). That is, the patient-engaging device 150 is operably engaged with a guidance device 200. The guidance device 200 is adapted to operably engage the mouth of the patient. For example, the engagement with the mouth of the patient may be through a splint 250 or other engaging member. In one instance, the splint 250 is configured to engage the patient's mouth in a "firm" or secure interaction (i.e., the splint 250 is engaged with the patient's teeth and does not move with respect to the patient's mouth). Since the splint 250 does not move with respect to the patient's mouth, the disposition of the splint 250 is known, and thus can be configured to provide a fiducial marker (i.e., a known origin or coordinate formed by the secure interaction with or otherwise associated with or attached to the splint 250) which can be used, for instance, to guide the patient-engaging device to prepare the site in the patient's mouth in association with the dental implant 300 (see, e.g., FIG. 1B). In one aspect, the splint 250 is configured to be "universally applicable" (i.e., capable of forming the secure engagement with the mouth of any patient), or at least applicable across a particular range of patients (i.e., one size fits a certain size or age of patient). In order to determine a reference associated with the fiducial marker, according to one aspect of the disclosure, the splint 250 may be engaged with the patient's teeth and the patient's jawbone structure then imaged using, for example, CT or any other suitable imaging technique such as, for instance, MRI. The fiducial marker can thus be established, for instance, as a reference origin of a relative coordinate system.

One skilled in the art will appreciate that the splint 250 may be configured in many different manners to accomplish the desired function as discussed herein. For example, the splint 250 may be rigidly attached to the patient's mouth in an appropriate manner depending on the condition of the patient. That is, if the patient has some strong teeth capable of supporting the splint 250, the splint 250 can be attached to the teeth with an adhesive or with a suitable clamp. For edentulous patients (i.e., without teeth), bone pins may be drilled through the splint 250 and into the patient's jawbone structure to fasten the splint 250 securely into place. The splint 250 may also be attached to the jawbone structure of any patient using, for example, appropriate bone screws. In one aspect, the positioning of the splint 250 with respect to the patient's mouth may not be critical or important, as long as the splint 250 remains rigidly in place. A fiducial marker (not shown) may then formed by the secure engagement, or may otherwise be attached to, or incorporated into, or associated with the splint 250, wherein the fiducial marker may be configured to have a geometry or other characteristic or feature that uniquely defines the fiducial marker in a three-dimensional space (i.e., such that the fiducial marker is readily identified in images of the patient's jawbone structure). In such instances, the fiducial marker may be comprised of, for example, a radiopaque material that can be clearly defined in the image (e.g., CT or MRI).

In one aspect, the patient-engaging device 150 may be engaged with an articulating arm member 350 (i.e., a robotic arm) which determines a range of motion of the patient-engaging device 150. The guidance device 200, in such instances, may further comprise a communication element 400 in communication between the splint 250 and the patient-engaging device 150 and/or the arm member 350. For example, the communication element 400 may comprise a mechanical linkage connecting the splint 250 to the patient-engaging device 150/arm member 350. That is, the communication element 400 may comprise, for example, a mechanically-tracked arm which attaches to the splint 250 engaged with the patient. In some instances, the arm may be attached to the splint 250 (rigidly and in a known, repeatable manner) with an attachment mechanism comprising a kinematic mount (i.e., a kinematic mount may be engaged between the arm and the splint 250). Attached to the patient in this manner via the attachment mechanism and the splint 250, the communication element 400 provides data (whether constantly, selectively, or otherwise as necessary) about the position of the patient (i.e., with respect to the fiduciary or fiducial marker) to the patient-engaging device 150/arm member 350, while still providing for accurate guidance thereof in the event that the patient moves. However, one skilled in the art will appreciate that the splint 250 and/or the fiducial marker determined thereby may be communicated to the patient-engaging device 150/arm member 350 in many different manners. For example, the fiducial marker may be communicated via a communication element 400 comprising a wireless transceiver, a hardwire connection, an optical communication system (i.e., a camera or other video device), an acoustic tracking system, or any other suitable mechanism, whether electrical, mechanical, electromechanical, acoustic, or optical in nature. That is, in various instances, the kinematic mount, itself, may comprise an attachment point for a tracking portion (or tracking arm or other tracking provision) associated with the guidance system for the surgical robot (i.e., wherein, for instance, reflective markers may be mounted to the attachment point for optical tracking of the fiducial marker or the splint device itself, or the attachment point may include a securing site for forming a mechanical connection therewith for mechanical tracking of the fiducial marker, or the attachment point may otherwise be configured to receive an appropriate element associated with any other suitable tracking arrangement for the fiducial marker). In other aspects, the kinematic mount may be configured or otherwise arranged to function as a fixed mounting site for particular tracking devices such as, for example, one or more markers that may be permanently affixed to the kinematic mount 500 and configured to be trackable by an optical-type tracking device (i.e., an optical tracking marker).

In any instance, the guidance device 200 may be further configured to include a controller device 450 (i.e., a computer device as shown in FIG. 3) for determining, controlling, or tracking the fiducial marker from the image of the patient's mouth having the splint 250 disposed therein, and for appropriately communicating the fiducial marker to the patient-engaging device 150/arm member 350. In some aspects, the controller device 450 may also comprise a planning device or otherwise include planning functionality for allowing a user to develop the virtual implantation plan, as otherwise disclosed herein, in conjunction with the hardware and/or software of the system 100.

In one aspect, the controller device 450 may be further configured to receive the image of the patient's jawbone structure (having the splint 250 therein). In some instances, the controller device 450 may be further configured to be capable of executing a planning routine that may comprise software, hardware, or a combination thereof (i.e., a planning device and/or planning functionality). The planning routine thus allows the practitioner to create, for example, a virtual implantation plan based on the captured image(s), whether in two dimensions or three dimensions, and to manipulate the image(s) of the patient's jawbone structure in conjunction with a "virtual implant" in order to develop the virtual implantation plan or placement determination of the prosthesis for the patient, in conjunction with a computerized model based on the image(s). In some aspects, the planning routine, virtual implantation plan, and/or placement determination may be created in relation, for example, to a coordinate system (relative or absolute), as will be appreciated by one skilled in the art, for associating the planning parameters with the fiducial marker. In other aspects, the controller device 450/planning device may include a peripheral device (i.e., a trackball or joystick in conjunction with, for example, 3D goggles, all not shown) to assist with or otherwise permit virtual manipulation of the placement of the virtual implant(s) with respect to the image(s) of the patient's jaw structure in order to, for example, align the implant(s) relative to each other or relative to adjacent teeth, to align the implant(s) relative to the affected nerve, and/or to align the implant(s) relative to the jawbone structure. The controller device 450/planning device may be further configured to perform such manipulation manually, automatically, or semi-automatically, as necessary or desired. Because the virtual implant(s) may be manipulated in a similar manner to the image(s), the orientation or placement of the virtual implant(s) may represent the desired actual placement of the implant with respect to the patient's jawbone structure, thus providing an intuitive interface for planning the implantation procedure.

In aspects where the splint 250/fiducial marker approach is used, the patient is automatically registered with the system 100 once the communication element 400 (arm) is attached to the splint 250 via the kinematic mount of the attachment mechanism. That is, the fiducial marker is automatically determined from the image(s) of the patient's jawbone structure, and the alignment and location thereof in physical space is known due to the kinematic mount connecting the arm to the splint 250. One skilled in the art will appreciate, however, that other alignment approaches may be implemented that do not necessarily require a fiducial marker. For example, in some instances, a surface matching technique can be implemented. More particularly, the patient's jawbone structure may be manipulated into a 3D configuration in the captured image(s). A suitable scanning device (i.e., a physical pointer or other imaging device such as an ultrasound transducer or OCT (optical coherence tomography) scanner may be attached to the end effector of the arm member 350 such that the tip of the arm member 350 is capable of scanning the patient's jawbone structure to "surface match" the captured and manipulated image(s) with an actual scan of the jawbone structure.

One skilled in the art will further appreciate that the association of the fiducial marker with the patient's anatomy, via the controller device 450, may be accomplished in different manners. For example, with respect to the registration of the image (e.g., CT scan) to the fiducial marker, one method could involve the jaw structure of the patient being imaged with the fiducial marker in place, as previously discussed, wherein the patient would then be substantially immediately subjected to the implantation procedure. Such a scheme may be beneficial, for example, in reducing the number of visits to the practitioner by the patient. However, in some instances, the practitioner may not have the imaging capabilities at hand, or may prefer to carefully determine the virtual implantation plan before carrying out the implantation procedure. In both such instances, the patient will likely be required to return to the practitioner at a later time. Accordingly, in such situations, a pre-operative imaging procedure (e.g., CT scan) may be performed on the jaw structure of the patient, without a fiducial marker in place (i.e., a "normal" scan by which the practitioner can determine the virtual implantation plan). This pre-operative imaging procedure can thus be performed, for example, at the practitioner's site, or at a dedicated scanning/imaging center. Subsequently, immediately prior to the implantation procedure being performed, and with the fiducial marker(s) engaged with the jaw structure of the patient, the practitioner may capture another image (e.g., CT scan, panoramic x-ray, or two single x-rays) of the patient's jaw structure. The controller device 450/planning device may thus also be configured to correlate the pre-operative image (used to determine the virtual implantation procedure) with the "day of" image so as to register the fiducial marker(s) with respect to the original pre-operative image. Such a registration or correlation procedure may be implemented in hardware, software, or a combination thereof, as will be appreciated by one skilled in the art. The implantation procedure could then proceed as otherwise disclosed herein.

In any instance, the communication element 400 is configured to engage the arm member 350 in a manner known to the system 100, such that the position/movement characteristics of the end effector are also known. This communication between the communication element 400 and the arm member 350 thus allows the patient-engaging device 150 to be registered with respect to the fiducial marker (or other reference with respect to the patient) attached to the patient via the splint 250, the kinematic mount, the communication element 400, and the arm member 350. In this manner, the virtual implantation process, planned through the controller device 450/planning device, may be accomplished in relation to the fiducial marker (or other reference with respect to the patient) and thus translated or otherwise communicated to the system 100 for directing the patient-engaging device 150.

The patient-engaging device 150 is disposed in or otherwise engaged with the end effector of the arm member 350 (robotic arm). The arm member 350 may be configured, for example, to provide six degrees of freedom and can also be configured to restrict or otherwise control the movement of the patient-engaging device 150. Further, the arm member 350 may have a miniature parallel structure to which the patient-engaging device 150 is secured and allowed to have full freedom of movement when not in cutting/preparation/implantation mode. Since the patient-engaging device 150 is attached to the end effector of the arm member 350, the patient interacting portion (i.e., the cutting/drilling tip) 500 (see, e.g., FIG. 2) of the patient-engaging device 150 must be in a known position (i.e., known to the system 100) relative to the arm member 350. In some aspects, in order to calibrate the interacting portion 500 of the patient-engaging device 150 with respect to the fiducial marker, a calibration element may be engaged with the patient-engaging device 150 via a kinematic coupling (i.e., rigidly mounted thereto in a known, repeatable manner). One skilled in the art will thus appreciate that the interacting portion 500 of the patient-engaging device 150 can then be calibrated with various tip calibrating methods (i.e., invariant point, etc.). Once calibrated, the calibration element is replaced with a cutting/drilling element in the patient-engaging device 150, in a known and repeatable manner, so that the calibration parameters (i.e., the position of the distal-most point and axis of cutting/drilling) associated with the interacting portion 500 are maintained as calibrated.

With the alignment with respect to the patient established and known by the system 100, and the virtual implantation plan developed through the controller device 450/planning device, the implantation procedure (i.e., cutting/drilling/insertion) can then be initiated by the practitioner moving the patient-engaging device 150 toward the patient's mouth (having the splint 250 engaged therewith). In such instances, the controller device 450/planning device is configured to control the movement of the patient-engaging device 150 via the arm member 350 such that the action of the practitioner merely moves interacting portion 500 (i.e., the cutting/drilling element) to the appropriate starting position for the implantation procedure, with respect to the patient's jawbone structure, as determined by the controller device 450/planning device and dictated by the virtual implantation plan. Once the cutting/drilling element is in the position dictated by the controller device 450/planning device, the invasive portion of the procedure can then be initiated, wherein the controller device 450/planning device may further dictate other parameters of the implantation device 150 such as, for example, the orientation of the path of the cutting/drilling element and the cutting/drilling distance along that path from the cutting/drilling origin, also according to the virtual implantation plan. In these instances, one distinction of the system 100 disclosed herein is that the patient-engaging device 150 is not guided by the practitioner, but is only urged by the practitioner along a procedural route determined via the virtual implantation plan and implemented via the controller device 450/planning device and the arm member 350. That is, the system 100 may be configured to restrict the practitioner to performing the implantation procedure with respect to the patient, as determined via the virtual implantation plan and implemented via the controller device 450/planning device and the arm member 350, whereby the controller device 450/planning device controls the allowable movement of the arm member 350 (and thus the patient-engaging device 150) in accordance with the virtual implantation plan created from the image(s) of the patient's jawbone structure. For instance, the system 100 may be configured for restricted movement of the arm member 350/patient-engaging device 150, as communicated to the practitioner through tactile/haptic feedback, where, for example, the arm member 350/patient-engaging device 150 may be easier to move according to the virtual implantation plan, and more difficult to move if deviating from the virtual implantation plan. One skilled in the art will also appreciate, however, that the physical structure of the arm member 350/patient-engaging device 150 may not necessarily be configured to provide full and absolute controlled movement according to the virtual implantation plan (i.e., due to vibration, flexing of components, and/or excessive force applied by the practitioner) and, as such, the system 100 may be further configured to provide other manners of feedback to the practitioner such as, for example, via a deviation warning indicia, haptic feedback, or any other suitable audio and/or visual and/or any other suitable mechanism. Therefore, the system 100 includes provisions for actually implementing the virtual implantation plan, and thus facilitates a more accurate implantation procedure, rather than merely warning the practitioner if any procedural parameters may be inaccurate. One skilled in the art will also appreciate, however, that, in some instances, the system 100 may be further configured to autonomously accomplish the virtual implantation plan, without the manipulation of the practitioner, through automatic manipulation of the arm member 350/patient-engaging device 150 via the controller device 450/planning device.

In one exemplary surgical procedure using a dental implantation system 100, as disclosed herein, the splint 250 (i.e., mouthpiece) is first attached to the patient's teeth, and thus provides or is associated with a fiducial marker. The patient's jawbone structure is then imaged (with the splint 250 in place and engaged with the patient's teeth) using, for example, CT or any other appropriate imaging technique (e.g., MRI), and the image(s) communicated with the controller device 450. The controller device 450 may be further configured to be capable of executing an implantation routine, thus allowing the practitioner to develop an implantation plan for the patient, for example, by manipulating a virtual implant with respect to the captured image(s). Once the virtual implantation plan is created, the communication element 400 is engaged with (i.e., attached to the patient's mouth, with the patient being positioned in a suitable position to initiate the procedure) or otherwise placed into communication with the splint 250. The arm member 350, patient-engaging device 150, and interacting portion 500 thereof, are then calibrated by the practitioner (or automatically by the controller device 450), before the actual cutting/drilling element of the patient-engaging device 150 is used by the practitioner (or autonomously via the controller device 450/planning device), via the patient-engaging device 150 as guided by the arm member 350 and the controller device 450, to accomplish the implantation procedure as planned and dictated by the virtual implantation plan.

According to other aspects of the present disclosure, a prosthetic member 600 (e.g., a denture, reproduction tooth, etc.) may be prepared or otherwise modified by the dental implantation system 100 to complementarily engage the dental implant previously implanted by the implantation system 100, by facilitating an aligned engagement therebetween. That is, the dental implantation system 100 may be configured to prepare the prosthetic member(s) 600 in a manner that allows the prosthetic member 600 to precisely correspond to and engage the dental implant, as planned and dictated by the virtual implantation plan, so that correct alignment therebetween is achieved when the prosthetic member 600 is permanently placed with respect to the dental implant within the patient's mouth. In one example, the interacting portion 500 (e.g., drill element) of the patient-engaging device 150 may be configured to and controlled by the controller device 450 to remove material from the prosthetic member 600 to form a borehole which is complementary to and configured to receive a corresponding portion of the dental implant, as shown in FIG. 4. For example, in one instance, the dental implant may extend beyond the jawbone/gum line of the patient so as to provide a post or projecting member upon which the prosthetic member 600 may be mounted, seated, or otherwise secured within the patient's mouth. Thus, the borehole of the prosthetic member 600 may be particularly formed by the dental implantation system 100 to facilitate alignment of the prosthetic member 600 with the dental implant.

In order to form the borehole in the appropriate location or site of the prosthetic member 600, the prosthetic member 600 may be registered with the implantation routine (i.e., registered with respect to the fiducial marker associated with the splint 250). In one instance, the prosthetic member 600 may be introduced within the virtual implantation plan and "virtually" registered with the system 100 in relation to the fiducial marker associated with the splint 250. In other instances, the prosthetic member 600 may be appropriately positioned within the patient's mouth at the time of the initial scan of the patient's jawbone structure, as previously described, so as to be physically registered with the fiducial marker associated with the splint 250. In such instances, the prosthetic member 600 may also have one or more fiducial markers (e.g., metallic bearing members) attached to, incorporated in, or otherwise associated therewith, wherein the prosthetic member fiducial marker(s) may be configured to have a particular geometry or other unique characteristic or feature that readily identifies and defines those fiducial marker(s) in the images of the patient's jawbone structure, as well as in comparison to the fiducial marker associated with the splint 250. As disclosed, the fiducial marker(s) associated with the prosthetic member 600 may be comprised of, for example, a radiopaque material that can be clearly defined in the image (e.g., CT or MRI). By implementing the prosthetic member fiducial marker(s), the configuration of the prosthetic member 600 with respect those fiducial marker(s) can be determined, and thus the system 100 can be configured and guided according to the prosthetic member fiducial marker(s) (i.e., according to a coordinate system associated with the prosthetic member 600 and registered with the system 100) so as to allow the patient-engaging device 150 to prepare the borehole at the appropriate site in the prosthetic member 600.

As a result of the imaging (and/or virtual implantation plan), the prosthetic member fiducial marker(s) may be identified in the imaging scans and then related to/registered with the system 100 so as to allow the borehole to be appropriately formed in the prosthetic member 600. That is, once the prosthetic member 600 is registered with or known to the controller device 450/planning device, the interacting portion 500 (or a calibration member), whether coupled to the patient-engaging device 150/arm member 350 or not, may be brought into engagement with the fiducial member(s) associated with the physical prosthetic member 600, with the prosthetic member 600 fastened or otherwise held in a static position, to associate the physical prosthetic device 600 with the system such that the borehole can be formed therein according to the virtual implantation plan. In any instance, the capability of preparing the prosthetic member 600 via the system 100 provides an expedited dental implantation process by facilitating a more accurate alignment between the dental implant and prosthetic member 600 (i.e., between an anchor portion and crown portion of a dental implant).

In another aspect of the present disclosure, in addition to preparing the prosthetic member 600 for the dental implantation process, the system 100 may be further configured to form, for example, the crown portion of the prosthetic member 600/dental implant itself. That is, in some aspects, the system 100 may be further integrated to include capabilities for preparing/forming the actual crown portion of the dental implant representing the form of the tooth/teeth to be implanted by fastening to the anchor portion of the prosthetic member 600. In such aspects, the system may further comprise, for example, a CAD/CAM milling system 700 such as shown in FIGS. 5A-5D, wherein the patient-engaging device 150, previously configured as a drill, cutter, or other site preparation device for preparing the site within the patient's mouth, may be interchanged with a milling device or other implant preparation device for machining the crown portion from a model or blank. More particularly, the controller device 450, including a processor, may be arranged as or to include a planning device (and/or planning functionality) having various standard models of teeth loaded therein or otherwise associated therewith, wherein, by way software, hardware, or a combination of software and hardware, a standard tooth model can be selected and customized by a user via the planning device, and the planning device then used to direct the CAD/CAM milling system 700, by way of the implant preparation device, to mill the selected tooth model to the specifications customized and saved by the user in the planning device. As such, the user (i.e., surgeon) using the planning device can plan the implant post (i.e., the anchor portion of a dental implant), as well as the crown (i.e., the crown portion of the dental implant) at the same time, and have the anchor portion and crown portion match each other with precision, as well as to be a reproduction or other appropriate representation of the particular prosthetic device selected for the site in the patient's mouth. The patient-engaging device 150, configured as a milling device or other implant preparation device for machining the crown portion from a model or blank, may then be interchanged with an implantation device for implanting the dental implant at the site within the patient's mouth. In this manner, by performing site preparation, implant preparation, and implantation with the same system 100, more desirable results may be obtained by way of a better correlation between the anchor portion and the crown portion of the dental implant, as well as the fit of the dental implant at the site within the patient's mouth.

Accordingly, in such aspects, the dental implantation system may comprise a site preparation device adapted to prepare a site within a mouth of a patient for receiving an anchor portion of a dental implant, and an implant preparation device configured to form a crown portion of the dental implant, the crown portion being configured to be received by the anchor portion, and the anchor portion securing the crown portion within the mouth of the patient. A guidance device, including a processor, may be configured to be in communication with a fiducial marker adapted to be engaged with the mouth of the patient. The guidance device is configured to interchangeably receive the site preparation device and the implant preparation device, and to guide one of the site preparation device and the implant preparation device, relative to the fiducial marker, in conjunction with manipulation of the one of the site preparation device and the implant preparation device by a user. A planning device, including a processor, is configured to be in communication with the guidance device. The planning device is further configured to determine an arrangement of the dental implant at the site in the mouth of the patient, to direct the site preparation device via the guidance device to prepare the site to receive the dental implant arrangement, and to direct the implant preparation device via the guidance device to prepare the crown portion for receipt by the anchor portion in accordance with the dental implant arrangement. The guidance device may also be configured to interchangeably receive an implantation device, in addition to the site preparation device and the implant preparation device, and to guide the implantation device, relative to the fiducial marker, and in conjunction with manipulation of the implantation device by the user, to implant the dental implant within the patient's mouth.

In another aspect, the planning of the surgical procedure by way of, for instance, the controller device 450 and/or the planning device and/or planning functionality associated therewith, may be enhanced by incorporating real-time feedback into the virtual implantation plan (i.e., as opposed to the virtual implantation plan being created solely based upon the imaging of the patient's mouth). For example, in such aspects, a drill, probe, or other instrument or patient-engaging device 150, whether engaged with the system 100 as disclosed herein or arranged separately in communication with the system 100 (i.e., tracked by camera or other optical device, attached to a mechanical arm having a known or trackable range of motion, tracked by an acoustic tracking, or otherwise maintained in communication with a reference point) may be manipulated by the user (i.e., surgeon) in relation to the site within the patient's mouth. In doing so, the manipulation of the patient-engaging device 150 by the user can be monitored in real-time by the controller device 450/planning device, in relation to the actual anatomy associated with the site within the patient's mouth or in relation to a model thereof. In such instances, the system 100 may also include a display device 800 (see, e.g., FIG. 6) in communication with the controller device 450/planning device, and configured to receive and display a real-time representation of the patient-engaging device 150 in relation to a representation of the mouth of the patient (i.e., the actual anatomy imaged during the manipulation or a model or other representation thereof otherwise determined) during manipulation of the patient-engaging device, such that the user can see or visualize feedback of the manipulation on the display device 800 in real time. That is, the dental implant position, the site within the patient's mouth, and/or the surgical (dental implantation) plan could be projected in a virtual manner on the display device 800, such that the user could visualize a simulation of the surgical procedure in relation to the physical manipulation of the patient-engaging device 150 by the user, and in real time. For example, an implantation device 150 having the prosthetic member 600 attached thereto may be moved or manipulated in relation to the site in the patient's mouth, and the user may concurrently view a representation of the implantation device 150 having the virtual dental implant engaged therewith on the display device 800, in relation to a virtual projection of the interaction of the dental implant with the site within the patient's mouth, while the manipulation is occurring.

In some instances, the controller device 450/planning device may be configured to relate the manipulation by the user to a previously-developed virtual implantation plan (or even initiate a virtual implantation plan based upon the manipulation), such that the virtual implantation plan can be updated and/or modified in relation to the manipulation by the user. Further, when a satisfactory "virtual" position of the dental implant is achieved, or at any point selected by the user, the virtual implantation plan can finalized or "locked in" by the user (i.e., the user can selectively indicate that the updates/modifications to the virtual implantation plan resulting from the manipulation are satisfactory, and the previously-existing virtual implantation plan can thus be updated/amended to include the same). In some particular aspects, the finalized virtual implantation plan may be executed by the controller device 450/planning device, with the system being configured to be responsive to the executed virtual implantation plan to direct manually guided patient-engaging device (i.e., using haptic or tactile feedback) or to direct an autonomous robotic system. In still other instances, the finalized virtual implantation plan may be applied in other manners such as, for example, in manufacturing a drill guide for directing the patient-engaging device 150 (configured as a drill). In such instances, since no invasive procedure was made in regard to the patient, to track the instrument and plan live on the patient, the actual surgical procedure can be performed at another later time using the drill guide.

Accordingly, in such aspects, a dental implantation system may comprise a patient-engaging device adapted to interact with a site within a mouth of a patient, and a guidance device, including a processor, configured to be in communication with a fiducial marker adapted to be engaged with the mouth of the patient. The guidance device is configured to receive the patient-engaging device, and to guide the patient-engaging device relative to the fiducial marker, in conjunction with manipulation of the patient-engaging device by a user. A display device is configured to display a real-time representation of the patient-engaging device in relation to a representation of the mouth of the patient during manipulation of the patient-engaging device. A planning device, including a processor, is configured to be in communication with the guidance device and the display device. The planning device is configured to monitor manipulation of the patient-engaging device in relation to the mouth of the patient, at least partially via the guidance device, and to direct information associated therewith to the display device.

The planning device may be further configured to form a dental implantation plan associated with the mouth of the patient, and optionally, to update the dental implantation plan at least partially in real-time relation to the monitored manipulation of the patient-engaging device. The planning device may be further configured to finalize the dental implantation plan when further update thereof is not required. In other instances, the planning device may be further configured to guide the patient-engaging device in relation to the mouth of the patient according to the dental implantation plan, and/or to direct a preparation device to prepare a dental implant, according to the dental implantation plan, for implantation in the mouth of the patient.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A dental implantation system, comprising:
   a drill or cutter adapted to prepare a site within a mouth of a patient for receiving an anchor portion of a dental implant;
   a milling device or CAD/CAM milling system configured to form or shape an external surface of a crown portion of the dental implant from a tooth model or blank, the crown portion defining an internal borehole configured to receive the anchor portion therein, the anchor portion securing the crown portion within the mouth of the patient; and
   a controller including a processor and configured to be in communication via a communication element with a fiducial marker adapted to be engaged with the mouth of the patient, the controller being in communication with a robotic arm having an end effector configured to interchangeably receive the drill or cutter and the milling device or CAD/CAM milling system, the controller being configured to guide the end effector having the drill or cutter or the milling device or CAD/CAM milling system, relative to the fiducial marker, in conjunction with manipulation by a user of the end effector having the drill or cutter or the milling device or CAD/CAM milling system, the controller including planning functionality for determining an arrangement of the dental implant at the site in the mouth of the patient, for directing the drill or cutter via the controller, communication element, and fiducial marker to prepare the site to receive the dental implant arrangement, and for directing the milling device or CAD/CAM milling system via the controller, communication element, and fiducial marker to form or shape the external surface of the crown portion of the dental implant from the tooth model or blank such that the crown portion, upon receipt of the anchor portion in the internal borehole defined thereby, is configured and placed in accordance with the dental implant arrangement.

2. A system according to claim 1, wherein the fiducial marker is formed by a splint device engaged with the mouth of the patient.

3. A system according to claim 1, wherein the robotic arm comprises an articulating arm member configured to determine a range of motion of the drill or cutter or milling device or CAD/CAM milling system.

4. A system according to claim 1, wherein the end effector is further configured to interchangeably receive an implanter, in addition to the drill or cutter and the milling device or CAD/CAM milling system, and the controller is configured to guide the end effector having the implanter, relative to the fiducial marker, and in conjunction with manipulation by the user of the end effector having the implanter, to implant the dental implant within the patient's mouth.

5. A dental implantation system, comprising:
a drill, cutter, or implanter adapted to interact with a site within a mouth of a patient;
a display device configured to display a real-time virtual representation of the drill, cutter, or implanter in relation to a virtual representation of the mouth of the patient during manipulation of the drill, cutter, or implanter; and
a controller including a processor and configured to be in communication via a communication element with a fiducial marker adapted to be engaged with the mouth of the patient, the controller being in communication with a robotic arm having an end effector configured to interchangeably receive the drill, cutter, or implanter, the controller including planning functionality for forming a plan associated with an interaction of the drill, cutter, or implanter with the site in the mouth of the patient, and being configured to guide the end effector having the drill, cutter, or implanter, relative to the fiducial marker, in conjunction with manipulation by a user of the end effector having the drill, cutter, or implanter and according to the interaction plan, the controller being in communication with the display and including planning functionality for monitoring manipulation of the drill, cutter, or implanter via the robotic arm and end effector in relation to the mouth of the patient, at least partially via the controller, and in relation to the communication element and fiducial marker, the controller determining position information for the drill, cutter, or implanter in real time from the monitored manipulation of the robotic arm and end effector and forming the real-time virtual representation of the drill, cutter, or implanter from the position information, and directing the real-time virtual representation of the drill, cutter, or implanter to the display device for display of the manipulation of the real-time virtual representation of the drill, cutter, or implanter in relation to the virtual representation of the mouth of the patient.

6. A system according to claim 5, wherein the controller includes planning functionality for updating the dental implantation plan at least partially in real-time relation to the monitored manipulation of the drill, cutter, or implanter.

7. A system according to claim 6, wherein the controller includes planning functionality for finalizing the dental implantation plan when further update thereof is not required.

8. A system according to claim 5, wherein the controller includes planning functionality for guiding the drill, cutter, or implanter in relation to the mouth of the patient according to the dental implantation plan.

9. A system according to claim 5, wherein the controller includes planning functionality for directing a preparation device to prepare a dental implant, according to the dental implantation plan, for implantation in the mouth of the patient.

10. A system according to claim 5, wherein the fiducial marker is formed by a splint device engaged with the mouth of the patient.

11. A system according to claim 5, wherein the robotic arm comprises an articulating arm member configured to determine a range of motion of the drill, cutter, or implanter.

12. A system according to claim 5, wherein the end effector is further configured to interchangeably receive a milling device or CAD/CAM milling system, in addition to the drill, cutter, or implanter, and the controller is configured to guide the end effector having the milling device or CAD/CAM milling system, relative to the fiducial marker, and in conjunction with manipulation by the user of the end effector having the milling device or CAD/CAM milling system, to form or shape a crown portion of a dental implant from a tooth model or blank, the crown portion being configured to be received by an anchor portion securing the crown portion within the mouth of the patient.

* * * * *